United States Patent [19]

Tomaiuolo

[11] Patent Number: 5,782,786
[45] Date of Patent: Jul. 21, 1998

[54] ADHESIVE BANDAGE DISPENSING SYSTEM AND SPOOL THEREFOR

[76] Inventor: Theodore J. Tomaiuolo, 114 Bohemia St., Plainville, Conn. 06062-2102

[21] Appl. No.: 720,949

[22] Filed: Oct. 4, 1996

[51] Int. Cl.$^6$ .................................................. A61F 5/00
[52] U.S. Cl. ........................ 602/41; 206/440; 206/441; 602/52; 221/25
[58] Field of Search ................ 602/41–59; 128/888, 128/889; 604/304; 206/441, 440; 221/25, 85

[56] References Cited

U.S. PATENT DOCUMENTS

| | | |
|---|---|---|
| 2,068,703 | 1/1937 | Powdermaker .................... 602/75 |
| 2,133,609 | 7/1938 | Eustis . |
| 3,530,494 | 9/1970 | Baratta . |
| 3,835,992 | 9/1974 | Adams, IV . |
| 4,666,040 | 5/1987 | Murata . |
| 4,751,133 | 6/1988 | Szycher et al. . |
| 4,807,753 | 2/1989 | Goldstein . |
| 4,832,008 | 5/1989 | Gilman . |
| 4,993,586 | 2/1991 | Taulbee et al. . |
| 5,065,894 | 11/1991 | Garland . |
| 5,133,477 | 7/1992 | Etheredge, III et al. . |
| 5,213,565 | 5/1993 | Rollband ....................... 602/52 X |
| 5,358,140 | 10/1994 | Pellegrino . |
| 5,543,270 | 8/1996 | Akao et al. ...................... 430/347 |

*Primary Examiner*—Richard J. Apley
*Assistant Examiner*—Kim Lee
*Attorney, Agent, or Firm*—Alix, Yale & Ristas, LLP

[57] ABSTRACT

An adhesive bandage dispensing system comprises a bandage retaining and dispensing spool and a continuous elongated bandage strip wound around the spool. The bandage strip comprises a plurality of individual adhesive bandages serially connected to one another at perforated edges. The perforations are oriented transverse to the elongated direction of the bandage strip and structurally weaken the bandage strip so that individual bandages may be separated from the bandage strip at the perforation lines by application of removal force thereto. The bandage strip is sized and shaped to ensure that absorbent pads of the bandage strip are sealingly enclosed by the bandages strip itself. The invention, thus, provides a bandage dispensing system which prevents contamination of the individual bandages without the need for additional packaging materials. Numerous advantageously shaped spools for use in the bandage dispensing system are disclosed.

14 Claims, 3 Drawing Sheets

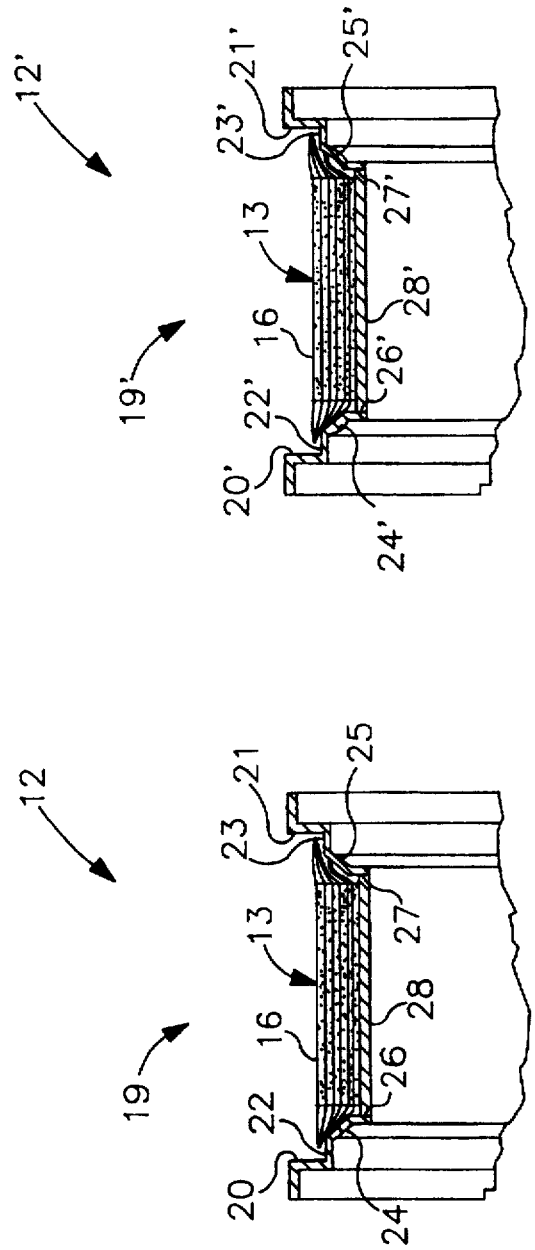

ADHESIVE BANDAGE DISPENSING SYSTEM AND SPOOL THEREFOR

BACKGROUND OF THE INVENTION

1. Field of the Invention

The present invention is generally directed to the field of adhesive bandages and, in particular, to facilitating the dispensing of adhesive bandages. More specifically, the invention is directed to a system for dispensing adhesive bandages from a spool having a strip of adhesive bandages wound thereon. Accordingly, the general objects of the present invention are to provide novel and improved methods and apparatus of such character.

2. Description of the Related Art

Smaller size bandages for finger wounds and the like are customarily packaged individually in paper with or without a tear string to facilitate opening the single bandage package. The bandage contained in the package ordinarily has its adhesive coated ends masked with plastic overlays which must be individually stripped off before the bandage is applied to the wound. A plurality of individually packaged bandages are usually contained in a paper or metal box having a hinged lid. With this conventional bandage packaging arrangement, the small bandages are awkward to manipulate. Particularly in an emergency, and frequently when an individual bandage is finally unpackaged for use, the adhesive end portions of the bandage can become twisted or adhered together. When this happens, the sterile pad between these end portions can become contaminated through contact with soiled fingers, the adhesive end portions or the like.

The prior art contains some teachings which are departures from the above-described conventional arrangement. One example of such departures in the prior art is U.S. Pat. No. 2,133,609, issued to Eustis on Oct. 18, 1938. This patent discloses spooled storage of bandages which involves a carrier strip wound on a spool body and an outer cover or sleeve into which the spool body is placed. While this patented disclosure represents a marginal improvement over the abovedescribed prior art packaging schemes, the devices disclosed therein still suffer from a number of deficiencies.

Among the largest of these deficiencies associated with the above-mentioned devices is the fact that the adhesive bandages wound on the spool bodies are first adhered to a sterile wrapping strip which must be removed from the adhesive bandage as the bandage is dispensed from the spool. Accordingly, a relatively complex and wasteful dispensing procedure is presented and this procedure yields an opportunity for inadvertently contaminating the sterility of the bandage. Use of these patented devices also generates unnecessary waste due to the need to dispose of the wrapping strip.

Therefore, there remains a need in the art for an adhesive bandage dispensing system which dispenses sterile adhesive bandages more effectively and efficiently than has heretofore been possible.

In particular, there remains a need in the art for an adhesive bandage dispensing system which preserves the sterility of the adhesive bandage without the need for additional packaging materials.

SUMMARY OF THE INVENTION

One object of the present invention is to provide an adhesive bandage dispensing system, whereby bandages can be quickly and easily dispensed and applied to a wound without the need to remove additional packaging material.

It is another object of the present invention to provide such an adhesive bandage dispensing system, whereby the bandages are sterile, familiar in form and effective in function, and whereby the dispensing system is cost-effective.

Still another object of the present invention is to provide an adhesive bandage dispensing system which promotes cost-effectiveness and reduces environmental waste resulting from discarded packaging.

Yet another object of the present invention is to provide a plurality of adhesive bandages readily available for use, thereby eliminating the tedious steps of breaking a bandage envelope and removing adhesive bandage backing materials.

It is still another objective of the present invention to provide an adhesive bandage dispensing system which ensures that the adhesive bandages dispensed therefrom remain sterile and contamination-free prior to usage without the need for additional disposable packaging materials.

Still another object of the present invention is to provide an adhesive bandage dispensing system which is capable of dispensing an elongated strip comprising a plurality of bandages which can be used as a bandage-affixing adhesive strip for dressing large wounds.

A further object of the present invention includes providing a spool for use in an adhesive bandage dispensing system which saves time, effort and aggravation in the dispensing, and application of adhesive bandages without sacrificing form, function, cost or the sterility of the bandages.

These and other objects and advantages of the present invention are achieved by providing an adhesive bandage dispensing system comprising a bandage retaining and dispensing spool and a continuous elongated bandage strip. The continuous bandage strip consists of a plurality of individual adhesive bandages connected to one another and wound about the bandage dispensing spool. A plurality of perforation lines which extend transverse to the elongated direction of the bandage strip are defined in the strip between adjacent bandages. The perforation lines structurally weaken the bandage strip so that individual bandages can be separated from one another at said perforation lines by application of a removal force thereto. Each of the individual bandages has a top surface and a bottom surface which is coated with an adhesive. Each bandage further comprises a sterile absorbent pad disposed on the bottom surface thereof. The bandage strip is wound about the spool such that the bottom surface of the bandages adhere to the top surfaces of other bandages and thereby seal the absorbent pads against contamination.

The objects and advantages of the present invention are also achieved in another embodiment by providing a spool for sealingly retaining and dispensing a plurality of adhesive bandages. In particular, the spool retains and dispenses bandages of the type having an absorbent pad disposed on an adhesive surface of a pad-carrier strip. The bandages are serially connected to form an elongated bandage strip. In accordance with this embodiment of the present invention, the spool comprises a hub which defines an axis having first and second opposite ends. Additionally, the spool includes first and second rims disposed at the first and second opposite ends of the hub such that the rims and hub cooperate to define a generally annular trough which extends about the hub axis. Additionally, the first and second rims define first and second sealing surfaces at the sides of the annular trough such that the sealing surfaces ensure sterility of the absorbent pads without the need for any additional materials by allowing selfsealing engagement between the various layers of the wound bandage strip. The sealing surfaces can be either linear or curvilinear in crosssection.

Numerous other advantages and features of the present invention will become apparent to those of ordinary skill in the art from the following detailed description of the invention, from the claims and from the accompanying drawings.

BRIEF DESCRIPTION OF THE DRAWINGS

The preferred embodiments of the present invention will be described below with reference to the accompanying Figures wherein like numerals represent like structures and wherein:

FIG. 3a is a partial cross-sectional view of the spool depicted in FIG. 2a; and

FIG. 3b is a partial cross-sectional view of the spool depicted in FIG. 2b.

DESCRIPTION OF THE PREFERRED EMBODIMENTS

Figure 1:
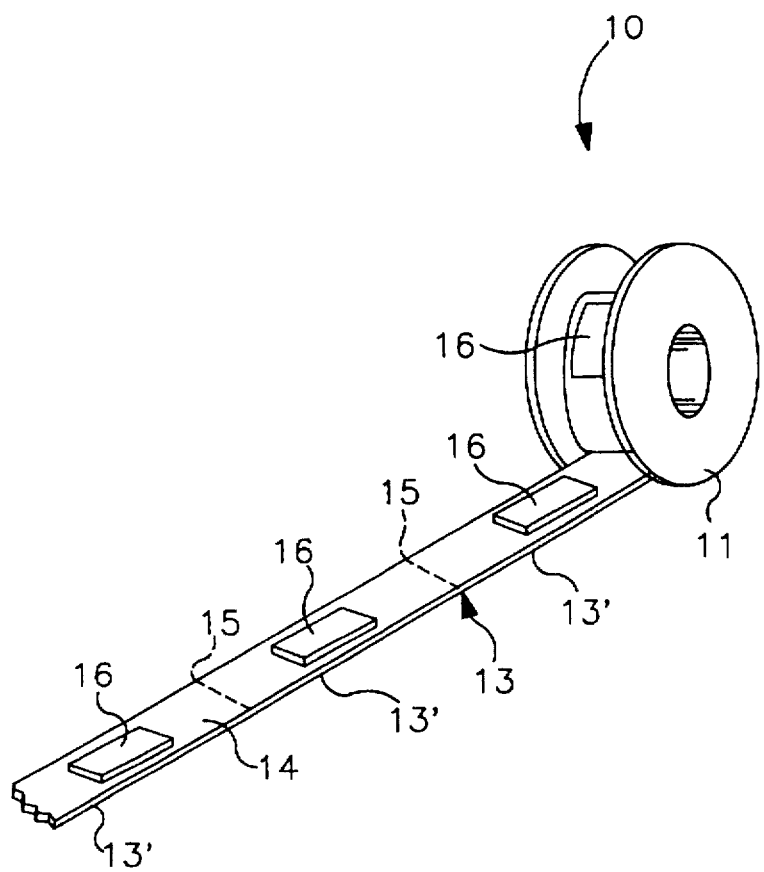
FIG. 1 is a perspective view of one preferred embodiment of the bandage dispensing system of the present invention.

One preferred embodiment of the adhesive bandage dispensing system will now be described with primary reference to FIG. 1. As shown therein, a bandage dispensing system 10 preferably comprises a spool 11 and a bandage strip 13 consisting of a plurality of individual bandages 13'. Each individual bandage 13' consists of an adhesive coated carrier strip 14 and an absorbent pad 16 disposed on the adhesive coated side of strip 14. As shown in FIG. 1, absorbent pads 16 are each preferably disposed entirely with the perimeter of individual bandage 13', i.e., both the width and the length of each absorbent pad 16 are less than those of the individual bandages 13'. Bandages 13' are in part defined by perforation lines 15 which structurally weaken bandage strip 13 so that the desired number of individual bandages 13'can be removed from spool 11 by applying a force in the elongated direction of bandage strip 13.

Bandage strip 13 is preferably wound about spool 11 such that an adhesive coated side thereof adheres to an opposite, non-adhesive, surface of bandage strip 13. It is to be noted that such an arrangement ensures that absorbent pads 16 of any given layer of bandage strip 13 is sealed by the pad carrier strip 14 of the succeeding layer. Therefore, the sterility of absorbent pads 16 can be preserved against contamination without the need for any additional packaging materials.

In order to dispense bandages using bandage dispensing system 10, a user simply grasps spool 11 and unpeels the desired number of individual bandages 13' from bandage strip 13. The user then presses against the last individual bandage 13' on the roll at a point thereof which is just behind the respective perforation line 15. Finally, the user pulls the bandages 13'0 to be removed until bandage strip 13 separates along the respective perforation line 15. While a single bandage will normally be dispensed from spool 11 at any given time, a single strip comprising a plurality of bandages can be dispensed by the system of the present invention. This may be desirable, for example, in an emergency situation where the strip may be used as a strip of adhesive tape which affixes a gauze bandage to a wound which is too large to be amply covered by any one of absorbent pads 16.

Figures 2A, 2B:
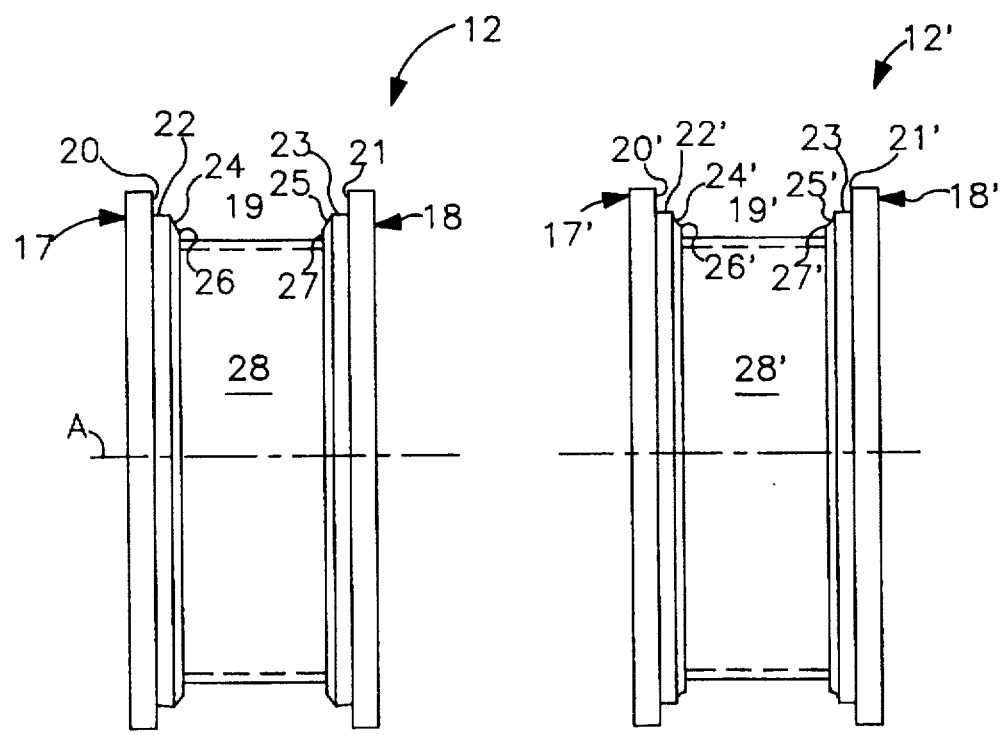
FIG. 2a is a front elevation view of one preferred embodiment of the spool of the present invention.
FIG. 2b is a second preferred embodiment of the spool of the present invention.

With reference now to FIGS. 2a and 3a, one modified and preferred form of spool 11 is shown generally at 12. In this embodiment, spool 12 includes a hub 28 having first and second opposite ends and first and second rim members 17 and 18 located at the opposite ends of hub 28. First and second rims 17 and 18 each comprise a plurality of surfaces and cooperate to define the particular shape of annular trough 19. As shown, first rim 17 preferably includes an inner hollow circular surface 26, a sealing surface 24, a cylindrical surface 22 and an outer hollow circular surface 20. As shown in FIG. 2a, these surfaces are coaxially disposed about hub axis A. Similarly second rim 18 preferably includes an inner hollow circular surface 27, a sealing surface 25, a cylindrical surface 23 and an outer hollow circular surface 21. As with the surfaces of rim 17, the surfaces are all preferably coaxially disposed about hub axis A.

As illustrated in FIGS. 2a and 3a, first and second rims 17, 18 cooperate with hub 28 to define an annular trough 19 therebetween. Therefore, annular trough 19 is also coaxially disposed about hub axis A. As shown in FIG. 3a, trough 19 is sized and shaped to receive bandage strip 13 therein. Preferably, the distance between inner hollow circular surfaces 26 and 27 is approximately equal to the width of absorbent pads 16. Since sealing surfaces 24 and 25 extend outwardly from inner hollow circular surfaces 26 and 27, thus defining a diverging trough section, the distance between sealing surfaces 24 and 25 are also approximately the same width as absorbent pads at a bottom edge thereof. As can be seen from FIG. 3a, when bandage strip 13 is wound about trough 19, the diverging trough section applies a force to the bandage strip in the edge regions adjacent each pad whereby each successive layer of bandage strip 13 seals the absorbent pad(s) 16 of the preceding layer by sealingly adhering to the preceding layer along sealing surfaces 24 and 25. The sterility of absorbent pads 16 can be ensured by such a configuration. Finally, it should be noted that the distance between outer hollow circular surfaces 20 and 21 is preferably approximately equal to the width of carrier strip 14. Thus, bandage strip 13 will normally not be wound more than a few layers above cylindrical surfaces 22 and 23.

In the embodiment of FIGS. 2a and 3a, sealing surfaces 24 and 25 take the form of oppositely facing frustoconical surfaces which are coaxially disposed about hub axis A. Surfaces 24 and 25 are, in the embodiment being described, generally linear in cross-section. While surfaces 24 and 25 could diverge away from one another at one of a wide variety of angular orientations, these surfaces preferably diverge at an angle of approximately 45°.

Turning now to the embodiment of FIGS. 2b and 3b, yet another modified version of spool 11 is depicted generally at 12'. As shown therein, spool 12' includes a hub 28' and first and second rims 17' and 18'. It is to be noted that while hub 28' is substantially identical to hub 28, rims 17' and 18' are only substantially similar to rims 17 and 18. It will also be noted that while surfaces 20'-23', and 26'-27' are substantially identical to surfaces 20-23 and 26-27 respectively, surfaces 24' and 25' are contoured differently from surfaces 24 and 25. Specifically, it should be noted that while surfaces 24 and 25 are linear in cross-section, surfaces 24' and 25' are curvilinear in cross-section. Therefore, aside from modifying surfaces 24 and 25 to assume the concave configuration of surfaces 24' and 25', spool 12' is substantially identical to spool 12. Accordingly, the cooperation between bandage strip 13 and spool 12' is substantially identical to that between bandage strip 13 and spool 12.

While the present invention has been described in connection with what is presently considered to be the most practical and preferred embodiments, it is to be understood the invention is not limited to the disclosed embodiment. Rather, the present invention also encompasses various modifications and equivalent arrangements included within the spirit and scope of the appended claims. For example, it is to be noted that sealing surfaces 24 and 25 could extend directly from hub 28 to the top of rims 17 and 18 respectively. Similarly, sealing surfaces 24' and 25' could extend from hub 28' to the top of rims 17' and 18' respectively.

What is claimed is:

1. An adhesive bandage dispensing system comprising:
   an axis-defining bandage retaining and dispensing spool having trough; and
   a continuous elongated bandage strip wound on said spool in said trough and around said axis, said bandage strip comprising a plurality of individual adhesive bandages connected together to form said bandage strip, each of said bandages having a carrier strip with a top surface and an oppositely disposed bottom surface, said carrier strip having an axial width and being coated on the bottom surface with an adhesive, each of said bandages further having an absorbent pad disposed on said carrier strip bottom surface, said pad having an axial width which is less than the axial width of said carrier strip bottom surface and a length which is less than the length of said carrier strip whereby said pad is surrounded by exposed adhesive coated areas of said bottom surface;
   wherein said spool comprises:
      a hub having first and second opposite ends said hub defining said axis; and
      first and second rims said first and second rims being respectively disposed at said first and second ends of said hub and having first and second sealing surfaces extending radially outwardly from said hub and diverging axially away from one another to thereby define said trough, said trough extending about said axis and having a varying width which, at a bottom portion thereof, is at least equal to the axial width of said absorbent pads and less than the axial width of said carrier strip whereby said diverging sealing surfaces apply a force to the bandage strip in an edge region adjacent each absorbent pad and whereby each successive winding of th e bandage strip seals the absorbent pad of each adhesive bandage to a preceding bandage along said sealing surfaces.

2. A dispensing system as recited in claim 1, wherein said trough has a top end and is axially wider than said absorbent pads at said top end.

3. A dispensing system as recited inn claim 2, wherein said sealing surfaces are curvilinear in cross-section.

4. A dispensing system as recited in claim 3, wherein said sealing surfaces are concave in cross-section.

5. A dispensing system as recited in claim 1, wherein said sealing surfaces are frusto-conical surfaces which are oriented coaxially with said axis.

6. A dispensing system as recited in claim 1, wherein said sealing surface are curvilinear in cross-section.

7. A dispensing system as recited in claim 6, wherein said sealing surfaces are concave in cross-section.

8. A dispensing system as recited in claim 1, wherein said rims respectively include first and second cylindrical surfaces extending from said sealing surfaces and oriented coaxially with said axis, wherein said first and second rims respectively include first and second hollow circular surfaces extending from said first and second cylindrical surfaces and oriented coaxially with said hub axis.

9. An adhesive bandage dispensing system comprising:
   a bandage retaining and dispensing spool comprising:
      a hub defining an axis and first and second opposite ends;
      first and second rims respectively disposed at said first and second opposite ends of said hub and having sealing surfaces extending from said hub and diverging away from one another to thereby define a trough which extends about said hub aixs; and
   a bandage strip, said bandage strip including an adhesive coated pad-carrier strip having first and second sides, a top surface and a bottom surface, sad pad-carrier strip being coated with an adhesive on said bottom surface, said pad-carrier strip also having means for periodically defining a plurality of perforation lines transverse to said bandage strip whereby said perforation lines and said first and second sides of said pad-carrier strip cooperate to define perimeters of a series of bandages, a plurality of absorbent pads periodically disposed on said bottom surface of said pad-carrier strip such that one absorbent pad is disposed inwardly of said perimeter of each of said bandages and is surrounded by an adhesive-exposed region thereof;
   said pad-carrier strip being wound around said spool in layered fashion such that said diverging sealing surfaces apply a force to the bandage strip in an edge region adjacent each absorbent pad and such that each successive winding of the bandage strip seals the absorbent pad of each adhesive bandage to a preceding bandage along said sealing surfaces.

10. A spool for sealingly retaining and dispensing a plurality of adhesive bandages of a type having an absorbent pad disposed on an adhesive side of a pad-carrier, the bandages being serially connected to form an elongated bandage strip having first and second opposite ends, the absorbent pad and the pad-carrier each having a width measured perpendicular to the elongated direction of the bandage strip, and the width of the pad-carrier being greater than the width of the absorbent-pad, said spool comprising:
   a hub, said hub defining an axis and first and second opposite ends; and
   first and second rims respectively disposed at said first and second opposite ends of said hub and having means defining sealing surfaces curvilinear in cross-section and extending from said hub and diverging away from one another to thereby define a trough which extends about said hub axis, said trough having a bottom with an axial width which is at least as axially wide as the width of the absorbent pads and less than the axial width of the pad-carrier.

11. A spool as recited in claim 10, wherein said trough has a top and is at least as axially wide as the pad-carrier strips at said top.

12. A spool as recited in claim 10, wherein said sealing surfaces are concave in cross-section.

13. A spool as recited in claim 10, wherein said sealing surfaces are concave in cross-section.

14. A spool as recited in claim 10, wherein said first and second rims respectively include first and second cylindrical surfaces extending from said sealing surfaces and oriented coaxially with said hub axis, wherein the axial distance between said hollow circular surfaces is at least as wide as the pad-carrier.

* * * * *